(12) United States Patent
Shimp

(10) Patent No.: US 7,645,458 B2
(45) Date of Patent: Jan. 12, 2010

(54) METHOD FOR STERILIZING AND/OR DEACTIVATING ADVENTITIOUS AGENTS ASSOCIATED WITH BIOLOGICAL MATERIALS

(75) Inventor: Lawrence A. Shimp, Morganville, NJ (US)

(73) Assignee: Osteotech, Inc., Eatontown, NJ (US)

( * ) Notice: Subject to any disclaimer, the term of this patent is extended or adjusted under 35 U.S.C. 154(b) by 276 days.

(21) Appl. No.: 10/614,448

(22) Filed: Jul. 7, 2003

(65) Prior Publication Data

US 2004/0048371 A1 Mar. 11, 2004

Related U.S. Application Data

(63) Continuation-in-part of application No. PCT/US02/00102, filed on Jan. 4, 2002.

(60) Provisional application No. 60/259,680, filed on Jan. 4, 2001.

(51) Int. Cl.
*A61F 2/28* (2006.01)
*A01N 1/00* (2006.01)
*A01N 1/02* (2006.01)
*C12N 13/00* (2006.01)
*B65B 55/00* (2006.01)

(52) U.S. Cl. .................. 424/423; 426/232; 435/1.1; 435/173.1; 435/366; 435/378

(58) Field of Classification Search .............. 424/423; 426/232; 435/1.1, 173.1, 366, 378, 379
See application file for complete search history.

(56) References Cited

U.S. PATENT DOCUMENTS

| | | | |
|---|---|---|---|
| 2,962,380 A | 11/1960 | Wertheim | |
| 4,538,757 A * | 9/1985 | Bertiger | 228/180.1 |
| 4,891,359 A | 1/1990 | Saferstein et al. | |
| 4,948,540 A | 8/1990 | Nigam | |
| 5,485,496 A | 1/1996 | Lee et al. | |
| 5,577,368 A | 11/1996 | Hamilton et al. | |
| 5,722,977 A | 3/1998 | Wilhelmy | |
| 5,730,933 A * | 3/1998 | Peterson | 422/22 |
| 5,753,182 A * | 5/1998 | Higgins | 422/23 |
| 5,782,914 A * | 7/1998 | Schankereli | 435/325 |
| 6,224,607 B1 | 5/2001 | Michelson | |
| 6,261,293 B1 | 7/2001 | Nicholson et al. | |
| 6,261,295 B1 | 7/2001 | Nicholson et al. | |
| 6,447,512 B1 | 9/2002 | Landry et al. | |
| 6,641,582 B1 | 11/2003 | Hanson et al. | |
| 6,692,501 B2 | 2/2004 | Michelson | |
| 6,755,839 B2 | 6/2004 | Van Hoeck et al. | |
| 6,840,941 B2 | 1/2005 | Rogers et al. | |
| 7,033,362 B2 | 4/2006 | McGahan et al. | |
| 7,083,625 B2 | 8/2006 | Berry | |

FOREIGN PATENT DOCUMENTS

| | | |
|---|---|---|
| DE | 26 25 289 A1 | 12/1976 |
| DE | 41 25 776 | 2/1993 |
| EP | 0 322 249 A2 | 6/1989 |
| EP | 0 341 007 B1 | 11/1989 |
| EP | 0 424 159 | 4/1991 |
| JP | 336585/1996 | 12/1996 |
| WO | WO 96 40297 | 12/1996 |
| WO | WO 98 31403 | 7/1998 |
| WO | WO 9831403 A * | 7/1998 |

OTHER PUBLICATIONS

The terms "substantial" and "fully"—Merriam-Webster Online Dictionary, at the web- http://m-w.com, pp. 1-2, accessed on internet on Nov. 17, 2006.
SU 561 564 A (Istranov L P), Jul. 1977, Patent abstract.

* cited by examiner

*Primary Examiner*—Jon P Weber
*Assistant Examiner*—Kailash C Srivastava
(74) *Attorney, Agent, or Firm*—Alicia G. Mills; Dorsey & Whitney LLP

(57) ABSTRACT

A method is provided for sterilizing and/or deactivating adventitious agent(s) on and/or within a biological material which comprises packaging the biological material, altering the original atmosphere associated with the biological material in order to reduce the level of oxygen to which the biological material is exposed and subjecting the packaged biological material with its altered atmosphere to irradiation.

17 Claims, No Drawings

METHOD FOR STERILIZING AND/OR DEACTIVATING ADVENTITIOUS AGENTS ASSOCIATED WITH BIOLOGICAL MATERIALS

CROSS REFERENCE TO RELATED APPLICATIONS

This application is a continuation-in-part of International Application No. PCT/US02/00102, filed Jan. 4, 2002, and claims the 35 U.S.C. § 119 (e) benefit of provisional application 60/259,680, filed Jan. 4, 2001. The entire contents of aforesaid application PCT/US02/00102 and 60/259,680 are incorporated by reference herein.

BACKGROUND OF THE INVENTION

1. Field of the Invention

This invention relates to a method for sterilizing and/or deactivating adventitious agents such as bacteria, viruses, etc., associated with biological materials, e.g., foods, tissue such as bone, etc., employing a combination of pre-irradiation and irradiation procedures.

2. Description of Related Art

It can be difficult to reduce the bioburden of a biological material, e.g., living tissue, many kinds of proteinaceous substances, drugs, etc., intended for medical/surgical application without negatively affecting the therapeutically useful properties of the material to a significant degree. For example, changes in pH, ionic strength or temperature can result in reversible or irreversible changes in the character of many kinds of biological materials and, consequently, a diminution in their therapeutic effectiveness. Attempts have been made to avoid or minimize irreversible changes to biological materials by sterilization employing ethylene oxide. However, ethylene oxide often reacts with proteins. In addition, because of the known tissue toxicity and the carcinogenic potential of the by-products of ethylene oxide, the United States Food and Drug Administration has set maximum residue limits for ethylene oxide and its major reaction products ethylene glycol and ethylene chlorohydrin.

Unlike ethylene oxide, radiation sterilization has the advantages of high penetrating ability, relatively low chemical reactivity and instantaneous effects without the need to control temperature, pressure, vacuum, or humidity. Radiation sterilization is a very convenient method for sterilizing medical devices, tissue, food, etc., and is widely used in industry. Both dosage levels and its biological effects are well known. It is generally believed that gamma-rays, electron beams, and x-rays as sources of ionizing radiation are equally effective in killing or deactivating microbial organisms. However, radiation can cause damage to the biological materials being sterilized. The damage can result from direct damage caused by the impact of radiation particles with proteins (resulting in broken chemical bonds), or, more commonly, from secondary reactions, usually activated oxygen, e.g., peroxides and oxygen radicals, that are generated by the interaction of the radiation and the material being sterilized. Many of these radicals are oxidizing in nature and do their damage by acquiring electrons from other substances resulting in cross-linking, radical chain reactions and bond breaking.

A variety of methods have been used to reduce or inhibit radiation damage. For example, bioburden is controlled to minimize the radiation dosage required for sterilization. Also, because oxygen is a major source of reactive species formed upon irradiation, removing oxygen from the material to be irradiated can reduce the amount of secondary damage. Oxygen removal is accomplished by evacuating and sealing the package, evacuating and backfilling the package with a less reactive gas and then sealing the package, or by flushing the package with a less reactive gas before sealing. The most frequently used less reactive gas is nitrogen, but others such as argon, etc. have also been used. Oxygen removal, while beneficial, is not completely effective because reactive species can be generated by the action of radiation on water, oxygen containing compounds, etc., that are part of the biological material being sterilized.

Other efforts to minimize the damage to biological materials caused by radiation sterilization have included the use of free-radical scavengers such as, e.g., tocopherol, citric acid, butylated hydroxyanisole, butylated hydroxytoluene, tertiary butylhydroquinone, propyl gallate, ascorbate, and other antioxidants that are "generally recognized as safe" by the Food and Drug Administration. However, these free-radical scavengers may also form undesirable reactive species as a result of the sterilization process.

Lowering the temperature at which sterilization is carried out has also been resorted to. Liquids, when present, are frozen. However, attempts using solutions or other compounds to minimize the effects of free-radical formation during sterilization have had limited success due to the immobility of the compound at the temperatures at which sterilization commonly takes places, e.g., $-70°$ C.

Thus, there remains a need for a method for protecting biological materials against the undesirable effects that frequently occur as a result of the sterilization process.

BRIEF SUMMARY OF THE INVENTION

It is an object of the invention to provide a method for reducing the bioburden of biological materials employing an irradiation procedure.

It is a further object of the invention to provide a method for reducing the formation of undesirable chemically reactive species within a biological material undergoing radiation sterilization.

It is still another object of the invention to provide a method for the radiation sterilization of therapeutically useful proteinaceous substances, food and/or living tissues such as allograft bone and bone-derived materials which contain a variety of biologically active proteinacious components.

It is still another object of the invention to provide a method for the radiation sterilization of a biological material, which prevents undesirable effects on the biomechanical strength of the biological material. For example, using the method of the invention may reduce undesirable effects on compressive strength, tensile strength or energy of the biological material.

It is still another object of the invention to provide a method for the radiation sterilization of a biological material, which prevents undesirable effects on the bioactivity of the biological material. For example, using the method of the invention may reduce undesirable effects on osteoinductivity, growth factor activity, signal transduction, translational activity and transcriptional activity of the biological material.

It is still another object of the invention to provide a method for the radiation sterilization of a biological material, which prevents undesirable effects on the in vitro degradation of the biological material. For example, using the method of the invention may reduce undesirable effects on soft tissue resorption and bone resorption of the biological material.

It is yet another object of the invention to provide a combined packaging and sterilizing method for a biological material.

In keeping with these and related objects of the invention, there is provided a method effective to protect a desired property of a biological material during the process of sterilization which comprises a) packaging the biological material;
b) providing a low oxygen atmosphere within the package
c) sterilizing the packaged biological material in the presence of said low oxygen environment effective to reduce and/or inactivate adventitious agent(s).

The method of the invention is conveniently utilized for the concurrent packaging and sterilization of a wide variety of biological materials. Thus, e.g., a package containing a biological material such as allograft bone for implantation, demineralized allograft bone, etc., can be evacuated and backfilled with hydrogen gas or mixture of hydrogen gas and a less reactive, preferably inert, gas such as nitrogen or argon and the contents of the package sterilized by exposure to ionizing and/or deactivating radiation such as gamma rays.

The expression "biological material" shall be understood herein to apply to any food or medically/surgically useful substance or device having a therapeutic action directly involving at least one biological mechanism and is to be distinguished from a biologically inert substance or device whose medical/surgical usefulness is essentially of a physical or mechanical character. Expressly excluded from the foregoing definition of "biological material" is a substance or device which is fabricated entirely from one or more biologically inert materials such as ceramic, synthetic polymer, etc., which when placed within the body is intended to function in a purely mechanical way, as for example, is the case with various kinds of prosthetic implants, surgical sutures, surgical clips, surgical meshes, fixation plates, fixation pins and screws, and the like.

The terms "osteogenic" as used herein shall be understood to refer to the ability of a material or substance to induce new bone formation via the participation of living cells from within the substance and "osteogenesis" as the mechanism or result.

The terms "osteoinductive" as used herein shall be understood to refer to the ability of a material or substance to recruit cells from the host which have osteogenic potential and the ability to form ectopic bone and "osteoinduction" as the mechanism or result.

The terms "sterilizing", "sterilization" and terms of like import shall be understood herein to mean a significant reduction in the bioburden of a biological material by the destruction and/or deactivation of adventitious agents such as microorganisms, particularly pathogenic bacterial and viral microorganisms, and polynucleotide fragments thereof present upon and/or within the biological material.

DETAILED DESCRIPTION OF THE INVENTION

The method of sterilizing and/or deactivating adventitious agents of the present invention is applicable to a wide variety of biological materials which can be liquid or solid or mixtures thereof, which include food, living tissues such as human donor bone for implantation, partially and fully demineralized bone materials prepared therefrom and devices and compositions containing such materials, proteins such as keratins, collagens, albumens, globulins, hormones, enzymes, peptides, polypeptides, simple and conjugated proteins such as glycoproteins, mucoproteins, lipoproteins, heme proteins and nucleoproteins, growth factors such as transforming growth factor, epidermal growth factor and platelet-derived growth factor, bone morphogenetic proteins, cells such as bone marrow cells and mesenchymal stem cells, and the like.

Especially preferred biological materials are the numerous known fully mineralized, partially demineralized and substantially fully demineralized autograft, allograft and xenograft cortical, cancellous and corticoncancellous bone implantable devices and compositions which possess osteogenic and/or osteoinductive properties.

The adventitious agent(s) which are sterilized and/or deactivated in accordance with the method of the invention include bacteria, mold, yeast, fungi, viruses, prions. Particular viruses that can be sterilized and/or deactivated are HIV, Hepatitis A, Hepatitis B and Hepatitis C, polio, herpes, parvo, west nile, SARS.

A preferred type of packaging system for use in the invention herein employs the so-called peel-open packages. These are constructed by heat-sealing two webs of packaging material around the edges. One layer is usually a plastic film of composite construction, that forms the heat seal, the other is a a moisture impermeable plastic or metal foil that forms a moisture and a microbial barrier. Alternatively, the opposing layer can be a formed plastic tray or blister. Shelf life is extended to a time that is determined by need rather than sterility protection. Whichever packaging method is used, provisions must be made for the opening of the package and the retrieval of the sterilized biological material in a manner that does not compromise its sterility.

In a variation of the packaging procedure, the biological material can be sealed in a porous package, the porous package then placed in an outer non-permeable package, thus treating the porous packaged product with its contents of biological material as the material to be sterilized. In a further variation, several porous packaged items can be placed in a common non-permeable package that is evacuated and backfilled with reducing atmosphere, e.g., hydrogen or hydrogen-inert gas mixture. The outer package can then be removed or retained as desired as long as the porous package still functions as a microbial barrier.

As an alternative to evacuation and backfilling, the package can simply be flushed with a reducing atmosphere, preferably with a hydrogen and inert gas mixture, prior to filling. However, this flushing technique does not remove trapped oxygen from the package as readily as the aforedescribed evacuation and backfilling operation. The hydrogen-gas packaged biological material can then be irradiated as described below.

Prior to packaging, the biological material can be subjected to one or more of the following optional procedures: (i) applying an antioxidant to the biological material, e.g., tocopherol, citric acid, butylated hydroxyanisole, butylated hydroxytoluene, tertiary butylhydroquinone, propyl gallate and ascorbate; (ii) removing lipid from the biological material, for example, employing a lipid-dissolving solvent, such as ethanol and/or at least one lipase; (iii) removing metal ions from the biological material, in particular, transition metals, employing one or more chelating agents such as aminopolycarboxylic acids, aminopolycarboxylic salts, diethylenetriaminepentaacetic acid (DTPA), nitrilotriacetate (NTA), diethylenetriaminepentaacetic acid (DTPMPA), ethylenediamine, N,N-bis(carboxymethyl)glycine, gluconates, organophosphonates, sodium silicate, magnesium sulfate, ferulic acid, sodium hydrosulfite, hydrogen peroxide, gluconic acid, anthraquinone, citric acid, dimercaprol, sodium hexametaphosphate, sodium citrate, sodium hexametaphosphate and ethylenediaminetetraacetic acid (EDTA); (iv) removing water from the biological material by such known and conventional methods as vacuum-drying, optionally accompanied by the application of mild heating, lyophilization of the biological material, displacement of water in the biological material with a hygroscopic liquid such as absolute alcohol;

and, (v) reducing the bioburden of the biological material, e.g., subjecting the biological material to an ionizing radiation dose of from about 2 to about 50 kGy and preferably from about 5 to about 25 kGy, subjecting the biological material to ultraviolet radiation of from about 1 nm to about 400 nm for from about 1 minute to about 1 hour and preferably from about 5 minutes to about 30 minutes, subjecting the biological material to pasteurization at from about 60 to about 120° C. for from about 1 minute to about 1 hour and preferably from about 90 to about 110° C. for from about 1 minute to about 5 minutes, and/or contacting the biological material with a bioburden-reducing amount of at least one antibiotic agent, antiviral agent and/or antimycotic agent selected from the group consisting of amphotericin B, gentamycin sulfate, imidazole compounds, azole compounds, such as ketoconazole, miconazole nitrate and aliphatic hydroxy acids, their salts and their glycols.

Following packaging of the biological material, it's original ambient atmosphere must be altered in order to remove or reduce the level of oxygen therein since the presence of oxygen can be harmful to the integrity of biological materials undergoing exposure to ionizing radiation. The original atmosphere associated with the biological material can be substituted with an inert atmosphere, a reducing atmosphere or mixture of inert and reducing atmosphere. The original atmosphere can also be removed by applying a vacuum to the package containing the biological material prior to sealing the package. Suitable vacuums can range from about 1 to about 200 torr.

The reducing atmosphere can contain at least one reducing gas such as hydrogen or carbon monoxide. Preferably, the reducing atmosphere is a mixture of at least one reducing gas and at least one inert gas. Inert gases that can be utilized include helium, neon, argon, krypton, xenon, nitrogen and carbon dioxide. Preferably, the mixture of reducing gas and inert gas will contain from about 0.5% to about 99%, and preferably from about 5% to about 30% reducing gas. The biological material can be exposed to the inert and/or reducing atmosphere for at least about 5 minutes up to about six months and, preferably from about one day to about two weeks prior to conducting the post-packaging irradiation step herein.

Optionally, the biological material with its altered atmosphere as previously described can be cooled or heated to levels which do not significantly degrade or affect the usefulness of the material. Thus, for example, the biological material can be cooled to a temperature ranging from just below ambient (about 25° C.) to −200° C. and preferably from about 0° C. to about −75° C. Cooling can be achieved in any known or conventional manner, for example, placing the packaged bone material in an enclosure such as refrigerator or freezer, contacting the packaged bone material with a cooling substance such as ice, ice and water mixture, solid carbon dioxide and liquid nitrogen. In the case of optional heating, temperatures on the order of from just above ambient to about 100° C. and preferably from about 30 to about 80° C. depending on the nature of the biological material can be utilized.

The step of irradiating the packaged biological material can be achieved by subjecting the biological material to a total dose of radiation of from about 2 to about 50 kGy and preferably from about 5 to about 25 kGy. If desired, the irradiation step can be conducted in a stepped or multiple dose fashion, for example, in a two-dose or three-dose sequence. The step of irradiating will ordinarily be carried out while the biological material is exposed to the reducing atmosphere and is in the (optionally) cooled or heated state.

When the biological material to be processed in accordance with the invention is bone, e.g., donor bone, the bone is preferably first defatted. Defatting can be achieved by any known or conventional process. Preferably, the bone is contacted with a defatting agent, preferably a liquid defatting agent to draw fat from the bone into the defatting agent, followed by separation of the defatting agent containing fat drawn from the bone from the defatted bone. Preferably, the defatting agent is a solvent for the fat contained in the bone. Solvents which can be used include aqueous ethanol which can optionally contain a non-ionic surfactant such as an alkylphenoxy polyethoxy ethanol, a commercially available example of which is Triton® X-100. Optionally, the defatting agent can contain a surfactant, preferably a non-ionic surfactant such as an alkylphenoxy polyethoxy ethanol. Defatting agent containing fat drawn from the bone can be separated from defatted bone by any suitable means, e.g., by centrifugation and decanting, preferably in a batch type centrifuge. If desired, defatting may be followed by desiccation, optionally under vacuum and at modestly elevated temperature if the nature of the biological material permits. Desiccation can be carried out about from about 0.9 torr to about 1 militorr and preferably from about 0.5 torr to about 0.1 torr.

Optionally the biological substance can be lyophilized (i.e. freeze-dried) employing procedures that are well known in the art.

The radiation employed in irradiating step (c) herein is typically an ionizing radiation, e.g., that provided as a beam of very high velocity, very small particles. The particles of the radiation beam interact with the biological material by colliding with the particles that make up the atoms of the material. That is, the particles of the radiation beam physically knock particles from atoms due to collision forces. These affected atomic particles are of two general classes, nuclear, which are found in the core of the atom, and electrons, which are found in the outer layers of the atom or molecule.

Nuclear particles consist of protons and neutrons. The energy required to disrupt nuclear particles is much greater than that found in chemical reactions and so nuclear particles are inert for chemical purposes. Disruption of the nucleus by radiation often makes the material permanently radioactive, and therefore sterilization radiation is held to energies below this threshold. Electrons participate in chemical reactions and much less energy is required to disrupt these than to disrupt the nuclear particles. All of the effects of sterilizing radiation are concentrated on the electrons. The effects of sterilizing radiation, therefore, are chemical in nature, resulting in new or altered chemical compounds, but not in radioactive substances.

The three types of ionizing radiation used herein are: gamma, electron beam (E-beam) and X-ray. Gamma radiation, usually from a cobalt 60 source, consists of very small particles (photons) which are fragments from the nucleus.

Gamma radiation is non-directional, i.e., it goes everywhere, and never shuts off. This property makes gamma radiation extremely dangerous to use. The advantage of gamma radiation is that it has high penetrating power (several centimeters), yet a low enough energy that the danger of nuclear changes in the material being irradiated is non-existent.

E-Beam radiation consists of electrons accelerated by an electric field. The energy depends on the magnitude of the accelerating voltage and energies are usually expressed in units of million electron volts (Mev). The advantage of E-beam over gamma rays is that, being electrically generated, the radiation is only present when the electric power is turned on. In addition, the beam is directional and its position can be easily controlled by electric and magnetic fields. The disadvantage is that electrons are very large compared to gamma particles so E-beams do not penetrate deeply (several millimeters at most) and are best suited for thin materials such as milk flowing over a plate in a shallow stream, or thin polymer constructs. In addition, high energy E-beams (over 10 Mev) can cause nuclear changes, so sterilizing doses are always set for a lower energy.

X-rays consist of nuclear particles (a type of photon) that are similar to gamma particles in their properties. X-rays are generated by a high energy electron beam hitting a metal target and ejecting X-ray particles (photons) from the nuclei of the atoms in the target. The energy of the beam depends on the target composition and the E-beam energy. Much power is wasted in converting an E-beam to X-rays. However, compared to the original electrons, the X-ray particles are smaller, therefore, they have a higher velocity and penetrate more deeply. For sterilization purposes, they are restricted to 5 Mev or less. X-rays, because of their greater penetrating power, are more suited for sterilizing larger, denser objects than E-beams. Yet X-rays still retain the advantages of being electrically generated.

The above discussion refers to the primary radiation source. However, the impact of a radiation beam also leads to secondary collisions, i.e., secondary radiation. The electrons ejected from the primary collisions go on to collide with other electrons, and these electrons collide with still more electrons. There is thus a cascade effect and electrons cause most of the collisions, no matter what the primary beam is composed of.

It is understood that biological materials can be effectively sterilized by gamma, electron-beam, or X-ray radiation. Common sources of photon radiation are gamma sources and X-ray sources. The reason that the sources of radiation may be interchanged is that both photons and electrons interact with matter by electrical ionization and excitation reactions. The mechanisms of the interactions of the gamma rays and X-rays are different from the interactions of electron beams. It is well known that gamma rays and X-rays are electromagnetic waves frequently referred to as photons. Having no electric charge or mass, photons transfer energy to materials mainly through Compton scattering and, at low energies, through photoelectric absorption. In contrast to photons, electrons have both mass and charge, so they interact readily with other charged particles, transferring their kinetic energy to materials via numerous elastic and inelastic collisions. Therefore, circumstances do exist where one or the other type of irradiation source (photon or electron) is preferred. For example, gamma sterilization or X-ray is often preferred when the bulk density of the material is high or when high-density regions may shield other parts of the material from exposure to electrons. Optionally, a multiple radiation dosing procedure, i.e., a two-dose approach can be used as well.

Although radiation has little direct effect on proteins, radiation damage to tissue can still occur due to secondary effects. In addition to direct hits by radioactive particles, damage can be caused by heating and the formation of free radicals. Heating tends to be a local effect and can be minimized by using evenly penetrating forms of radiation and not using excessive doses. Unfortunately, free radicals are much more difficult to control than heating. The secondary effects that damage tissue also theoretically enhance the effects of radiation in bringing about sterilization. However, controlling these effects to minimize radiation damage to desirable tissue has little practical effect on sterilization efficiency because dosage requirements are based only on the probability of direct hits on contaminating organisms. Secondary effects are too variable to be taken into account in official dose guidelines.

Radiation causes its damaging secondary effects primarily through the chemical activity of free radicals. The easiest to form radicals are oxygen, or oxygen containing radicals. Oxygen sources can be oxygen from the air, oxygen from water, or other oxygen containing substances. Oxygen radicals form peroxides, and the peroxides react readily with a large variety of substances. Such reactions often lead to cross-linking, which can alter the physical as well as the chemical state of proteins. Because configuration is just as important as chemical composition for protein function, cross-linking seriously damages proteins. In addition, if the oxygen is from an organic material, the site that the oxygen came from can also react and lead to further damage. Although the actual chemistry may be complex, it is not novel. Damage by radiation produced peroxides follows the same mechanisms as damage from sterilization by peroxide solutions or electrically generated ozone.

Radiation sterilization, as currently practiced, employs electron accelerators or radioisotopes. Electrons have relatively low penetration ability, and the use of accelerators requires careful control. Gamma-radiation sterilization usually employs $^{60}$Co and occasionally $^{137}$Cs as the radioisotope source. A very wide range of packaging materials can be used because gamma rays possess a considerably greater penetrating ability. However, they must not be degraded to the point where the quality of the aseptic barrier is compromised.

Although it is not entirely understood how a reducing atmosphere can act as a radical scavenging agent and/or reducing agent, the following theory is offered by way of a possible explanation. Radiation particles have a thermal energy level equal to several thousand ° C. and the radicals they produce also have thermal energies in the 1,000° C. range. The energies of the radicals and secondary ions are more than sufficient to initiate a reaction with a reducing atmosphere. It is in this way that a reducing atmosphere can help to control unwanted side reactions arising from sterilizing radiation. The reducing atmosphere acts as a reducing agent and radical scavenger that actively neutralizes destructive radicals as they form. The advantage to using a reducing atmosphere in the sterilization method herein is that a reducing atmosphere can help to neutralize destructive species that originate from within the irradiated biological material itself. Oxygen removal alone cannot address damage from these sources. A further advantage of using a reducing atmosphere is its ability to easily diffuse throughout most biological materials and therefore be present at the sites of radical formation, even in solidly frozen objects or high density objects such as donor bone for implantation. Hydrogen is useful as a reducing atmospheric gas because it remains in its gaseous state to temperatures as low as −259° C. at standard pressure. By contrast, at low temperatures, conventional antioxidants are frozen and immobile, so they cannot always be present at the sites of radiation damage (initiation and/or progression). Also, hydrogen's small size, i.e., a bond length of about 0.75, Angstroms allows it to penetrate the small pores of the item to be sterilized.

Because it remains mobile at low temperatures, the presence of reducing gas such as hydrogen or carbon monoxide during irradiation is especially advantageous in the case of biological materials which are chilled, or cooled, to below ambient temperature, e.g., at from about 10° C. to about −196° C. (liquid nitrogen) and preferably from about 0° C. to about −78° C. (solid carbon dioxide). Freezing the biological material, e.g., allograft bone or bone-derived product, prior to exposing the material to radiation can be a useful expedient to further guard against the formation of free radicals as the frozen material is undergoing irradiation.

Although hydrogen has a much higher activation energy compared to conventional antioxidants or radical scavengers, during irradiation, as explained above, there is more than enough energy to initiate a reaction with hydrogen. An advantage of hydrogen is that it is not destroyed by radiation; at worst it dissociates into hydrogen radicals that quickly recombine or form a harmless compound with a nearby organic material. By contrast, conventional organic antioxidants/radical scavengers can break into non-functional fragments, or, once fully oxidized, become very powerful oxidizing agents themselves.

The reducing gas employed herein can be combined with other gases, e.g., a less reactive, and preferably inert, gas such as nitrogen, carbon dioxide, helium, argon, xenon, and their mixtures. The individual gases are supplied commercially, e.g., in pressurized cylinders, or the gases can be premixed by the supplier. When diluted with a less reactive or inert gas, the reducing gas can be present at concentrations of from about 1 to about 99% by volume and preferably from about 5 to about 30% by volume.

The pressure of the reducing atmosphere can be at, above or below ambient. When the method of the invention is carried out upon a biological material contained within a package, e.g., as hereinafter described, elevated gas pressures can be employed up to those that can be withstood by the package system. In general, ambient pressure to pressures on the order of up to about 3 atmospheres can be utilized.

The method of the invention herein can be carried out by evacuating a package containing the biological material to be sterilized, backfilling the package with a reducing atmosphere, e.g., hydrogen or hydrogen in admixture with an inert gas, and sealing the package. The evacuation and backfilling cycles can be repeated any number of times. The package can be made of any reasonably non-porous material, though the less permeable the package is to the reducing atmosphere, the longer the delay can be from when the package is filled until the radiation process is carried out. The main purpose of packaging is to protect the sterility of the biological material contents. When a biological material is placed in a protective container or package and subsequently sterilized, the process is referred to as terminal sterilization. When the biological material is first sterilized and then placed in a presterilized container or package, the process is referred to as sterile filling. Packaging material used for terminal sterilization must permit full sterilant penetration as well as provide a microbial barrier. Consideration must also be given to the conditions to which the sterile package will be exposed until its contents are used such as storage, transportation, frequency of handling, etc.

Storage time by itself is not expected to affect the maintenance of sterility. However, longer storage time may increase the incidence of potentially harmful conditions. Frequent handling, wetness, and possible deterioration of the packaging material are typical examples of conditions that may compromise sterility and limit the shelf life of a package. The package contents may have a specific shelf life. The wide choice of packaging materials and methods available for industrial processes allows the selection of packaging materials, package designs, and processes that provide maximum protection. Indeed, with appropriate packaging, sterilization methods, and materials, sterility can be protected for an indefinite length of time.

Bioburden determinations can be carried out to determine a desired radiation dose. Thus, the dosage of ionizing radiation for a specific bioactive material can be experimentally determined by measuring the bioburden of the pre-sterilized material employing known and conventional procedures so as to provide a typical range of initial bioburden for the material and thereafter irradiating portions of the material at different dosage levels and again measuring bioburden following termination of each radiation exposure. Based on these experimental data, an optimum radiation dosage level can be determined for a specific biological material and target bioburden endpoint. In these experiments, radiation exposure can be monitored with biological indicators utilizing *Bacillus pumilus* as the test organism. Counters and electronic measuring devices can also be used. Chemical dosimeters based on ferrous sulfate, ferrous cupric sulfate, or ceric sulfate are also generally useful. Color-change process indicators may be used but these cannot measure the radiation dose.

In general, the radiation exposure whether for gamma rays, E-beam or X-rays, can range from about 5 to about 50 kGy and preferably from about 10 to about 40 kGy depending on the nature of the biological material to be sterilized, its initial bioburden and the desired bioburden endpoint.

When the step of altering the original atmosphere associated with the biological material is carried out by exposing the biological material to a reducing gas such as hydrogen alone or in combination with an inert gas, it can be advantageous to maintain contact of the biological material with the altered atmosphere gas even after irradiating step (c) has been terminated since the reducing gas will still continue to scavenge for any residual free radicals that may be present.

In the following Table, a number of embodiments of the method of the invention are presented which are advantageously applied to biological materials in general and bone, especially donor bone, in particular:

| Optional Treatment of Biological Material Before Packaging | Optional Reduction of Bioburden of the Biological Material | Step (a) of Packaging the Biological Material | Step (b) of Altering the Original Atmosphere | Optional Cooling or Heating | Step (c) of Irradiating the Biological Material |
|---|---|---|---|---|---|
| Application of Antioxidant | Ionizing Radiation Dose of Less Than 20 kGy | Any Packaging Material Impermeable to Gases | 100% Inert Atmosphere | −200 °C. to −125 °C. | Ionizing Radiation Dose of Less Than 2 kGy |

-continued

| | | | | | |
|---|---|---|---|---|---|
| Defatting with Solvent and/or Lipase | Ionizing Radiation Dose of More Than 20 kGy | Any Packaging Material Impermeable to Microbes | 100% Reducing Atmosphere | −125° C. to −75 ° C. | Ionizing Radiation Dose of Less Than 5 kGy |
| Application of Chelating Agent for Removal of Metal Ions | Ultraviolet Radiation | Any Packaging Material Permeable to Gases | Mixture of Reducing and Inert Atmosphere | −75° C. to 0° C. | Ionizing Radiation Dose of Less Than 10 kGy |
| Application of Chelating Agent for Removal of Transition Metal Ions | Pasteurization | Addition of Secondary Packaging Impermeable to Gases | Vacuum/ No atmosphere | 0° C. to 25° C. | Ionizing Radiation Dose of Less Than 20 kGy |
| Removal of Water by Vacuum Drying, Optionally, at Elevated Temperature | Addition of Antibiotic Agent | Addition of Secondary Packaging Impermeable to Microbes | | 25° C. to 50° C. | Ionizing Radiation Dose of Less Than 30 kGy |
| Removal of Water by Lyophilization | Addition of Antiviral Agent | Addition of Secondary Bulk Packaging Impermeable to Gases | | 50° C. to 75 ° C. | Ionizing Radiation Dose of Less Than 40 kGy |
| Removal of Water by Displacement with Another Liquid | Addition of Antimycotic Agent | Addition of Secondary Bulk Packaging Impermeable to Microbes | | 75° C. to 100° C. | Ionizing Radiation Dose of Less Than 50 kGy |

The foregoing description of the preferred embodiments of the present invention have been presented for purposes of illustration and description. These embodiments are not intended to be exhaustive or to limit the invention to the precise forms disclosed, and obviously many other modifications and variations are possible in light of the above teachings. The embodiments were chosen and described to best explain the principles of the invention and its practical applications, thereby enabling others skilled in the act to best utilize the invention in its various embodiments and with various modifications as are suited to the particular use contemplated.

The following examples are illustrative of the method for sterilizing a bioactive material in accordance with the invention.

EXAMPLE 1

Posterior intervertebral ramp implants are produced in a clean room environment from human femurs. The finished implants are washed in 70% ethyl alcohol, lyophilized (freeze-dried) and placed in individual tray packages.

Each tray is placed in an Audionvac sealing apparatus (Audion Electro B.V., Weesp-Holland) which is supplied with a cylinder consisting of 6/94 hydrogen/argon gas. Before the tray packages are sealed, they are evacuated and back-filled with the gas mixture twice. Following sealing, the gas mixture remains in each tray package.

The packaged implants are then sealed packages and then treated with 15 kGy gamma radiation from a cobalt 60 source to reduce the bioburden of the implants to the desired levels.

EXAMPLE 2

Posterior intervertebral ramp implants as described in Example 1 are placed in individual tray packages provided with porous lids to provide ready transfer of gases out of and into the packages. The tray packages are then placed in an Audionvac sealing apparatus supplied with a source of substantially pure nitrogen gas. Each tray is evacuated and back-filled with nitrogen gas twice to replace the air (containing oxygen) with essentially pure nitrogen gas. Each sealed tray is then placed in a second larger tray, the trays are placed in an Audionvac sealing apparatus supplied with a source of substantially pure hydrogen. The trays are evacuated and back-filled twice with hydrogen gas before being sealed. This step results in each sealed package possessing a hydrogen-rich atmosphere which diffuses into the implant contained therein. Irradiation of the tray packages is then carried out as described in Example 1.

EXAMPLE 3

A series of 18 struts (9 pairs) were cut from a human femoral shaft. The strut dimensions were 4.0×4.0×40 mm. Each strut was smoothed with a Buehler grinder.

All struts were freeze-dried using a 19 hour cycle, then packaged in heat sealed foil pouches either in air or in a 70/30 Argon-hydrogen atmosphere. Pouches filled with the 70/30 ArH$_2$ gas were sealed inside a Glove bag that was filled with the ArH$_2$ gas. The control samples in groups of three from each set were not irradiated. The remaining samples (three from each set) were irradiated at ambient temperature. Irradiation was carried out to achieve a total dose of 30 kGy.

Mechanical strength was assessed using a 3-point bending test. Load to failure and energy at failure were recorded. All struts were rehydrated in saline for 21 hours before testing. The results for failure load and energy to break are presented in the Table 1 in terms of percent relative to the control samples.

TABLE 1

| Sample | Total Radiation Dose, kGy | Failure Load, relative to control | Failure Energy, relative to control |
|---|---|---|---|
| control | 10 | 100% | 100% |
| Air, ambient | 30 | 37% +/− 9% | 12% +/− 5% |
| ArH$_2$, ambient | 30 | 60% +/− 7% | 47% +/−14% |

The ArH$_2$ atmosphere provided a significant protective effect compared to the air packaged samples. Especially interesting is that the failure energy was proportionally better preserved than the failure load. Failure energy is a measure of brittleness, which can be brought about by radiation induced cross-linking. This appears to be a clear illustration of the effectiveness of hydrogen in preventing radiation induced cross linking.

EXAMPLE 4

The experiments in example 3 were repeated, only this time 12 struts were cut and the struts were divided into struts 3 at ambient temperature and chilled struts 3. The cooled samples were placed in a Styrofoam cooler box and were packed with dry ice before being sent to a remote location for irradiation. Upon receipt after irradiation, it was confirmed that dry ice was still present. The results of the irradiation are presented in Table 2.

TABLE 2

| Sample | Radiation Dose, kGy | Failure Load, relative to control | Failure Energy, relative to control |
|---|---|---|---|
| Control | 0 | 100% | 100% |
| Air, ambient | 30 | 35% +/− 8% | 20% +/− 4% |
| ArH$_2$, dry ice | 30 | 76% +/− 16% | 90% +/− 42% |
| Air, dry ice | 30 | 67% +/− 20% | 46% +/− 7% |

The ArH$_2$ atmosphere again provided a significant protective effect compared to the air packaged samples, especially when looking at energy (brittleness). The air irradiated samples showed much less strength damage when chilled, however, the energy decrease of the chilled samples was still about the same as the ambient temperature samples. The ArH$_2$ protected samples were hardly affected by chilling (compared to ambient temperature irradiation, Example 3). It was therefore concluded that the ArH$_2$ protective atmosphere by itself was as effective or more effective in preventing radiation damage than chilling with dry ice alone, but that protection can be increased by combining chilling with an ArH$_2$ atmosphere.

EXAMPLE 5

A total of 9 struts were cut from each of three separate donor femurs. The struts were cut so their length is oriented parallel to the long axis of the shaft, and each strut is 4 mm×4 mm×40 mm long.

Three struts from each of the donors were defatted by soaking overnight in a 50/50 mixture of chloroform and methanol. All struts were then frozen for 6 hours, and lyophilized together for 18 hours, the first 6 hours being at −50 degrees C., the remaining time being at 30 degrees C. Three undefatted struts from each donor were packaged together in a foil pouch and kept as controls. The remaining six struts (three defatted, three not defatted) from two of the donors were packaged individually in foil pouches in air. For the third donor, six struts (three defatted, three not defatted) were packaged separately in foil pouches in a glove bag filled with a 50/50 mixture of argon and hydrogen. This argon/hydrogen atmosphere was thus captured inside of the sealed pouches.

All but the control struts were irradiated at 22 to 23 kGy. Irradiation was carried out with cobalt 60 radiation.

All of the struts were tested in three point bending using an MTS machine at a crosshead speed of 5 mm/minute. Breaking stress and energy to break were recorded. (Energy is a measure of brittleness, low energy meaning more brittle.) All of the data were normalized to the corresponding controls so the results are reported in units of % relative to the control.

The results presented in Table 3 show that without the protection of the hydrogen containing atmosphere, the 21 to 23 kGy radiation dose had a very negative effect on mechanical strength regardless of whether or not the struts were defatted. The defatted Ar/H$_2$ packaged struts showed no significant changes in mechanical properties. The nondefatted Ar/H2 packaged struts showed some decrease in mechanical properties (especially energy), but the decrease was small compared to the air packaged strut decreases. These data show that the hydrogen-containing atmosphere provided a significant protective effect.

TABLE 3

| Donor | treatment | Radiation dose, Mrad | Stress (%) | Energy (%) |
|---|---|---|---|---|
| A, B | Control | 0 | 100 | 100 |
| | Defatted, air packaged | 2.1-2.3 | 51 +/− 4 | 20 +/− 5 |
| | Not defatted, air packaged | 2.1-2.3 | 57 +/− 6 | 23 +/− 5 |
| C | Control | 0 | 100 | 100 |
| | Ar/H$_2$ packaged, defatted | 2.1-2.3 | 98 +/− 7 | 89 +/− 16 |
| | Ar/H$_2$ packaged, not defatted | 2.1-2.3 | 74 +/− 21 | 46 +/− 35 |

What is claimed is:

1. A method effective to protect one or more properties of a biological material or device containing said biological material during the process of sterilization which comprises:
    a) packaging the biological material;
    b) providing a protective atmosphere within the package, wherein providing a protective atmosphere within the package of the packaged biological material is carried out by: removing an original atmosphere under vacuum and replacing the original atmosphere, wherein removing and replacing is done by evacuating and backfilling the original atmosphere in the package, flushing the original atmosphere in the package, or substituting the original atmosphere in the package, and wherein replacing the original atmosphere is done with a protective atmosphere comprising a reducing atmosphere or a mixture of an inert atmosphere and a reducing atmosphere, wherein the mixture of an inert atmosphere and a reducing atmosphere contains about 0.5 to about 99% by volume reducing atmosphere;
    c) sterilizing the packaged biological material or device containing said biological material in the presence of said protective atmosphere to reduce and/or inactivate an adventitious agent or adventitious agents.

2. The method of claim 1, wherein the inert atmosphere comprises nitrogen.

3. The method of claim 1, wherein the reducing atmosphere comprises at least one reducing gas selected from the group consisting of hydrogen and hydrogen sulfide.

4. The method of claim 1, wherein the mixture of inert atmosphere and reducing atmosphere contains from about 5 to about 30% by volume reducing atmosphere.

5. The method of claim 1, wherein the original atmosphere is removed under a vacuum of from about 1 to about 200 torr.

6. The method of claim 1, wherein the biological material is bone.

7. The method of claim 1, wherein the biological material is selected from the group consisting of food, tissue and therapeutically useful substance.

8. The method of claim 1, wherein the inert atmosphere comprises argon.

9. The method of claim 1, wherein the inert atmosphere comprises helium.

10. The method of claim 1, wherein the inert atmosphere comprises neon.

11. The method of claim 1, wherein the inert atmosphere comprises krypton.

12. The method of claim 1, wherein the inert atmosphere comprises xenon.

13. The method of claim 1, wherein the inert atmosphere comprises carbon dioxide.

14. The method of claim 1, wherein removing and replacing is done by removing an original atmosphere under vacuum and replacing the original atmosphere with a reducing atmosphere or a mixture of an inert atmosphere and reducing atmosphere, wherein the mixture of an inert atmosphere and a reducing atmosphere contains about 0.5 to about 99% by volume reducing atmosphere.

15. The method of claim 1, wherein removing and replacing is done by evacuating an original atmosphere under vacuum and replacing the original atmosphere with a reducing atmosphere or a mixture of an inert atmosphere and reducing atmosphere, wherein the mixture of an inert atmosphere and a reducing atmosphere contains about 0.5 to about 99% by volume reducing atmosphere.

16. The method of claim 1, wherein removing and replacing is done by substituting an original atmosphere under vacuum and replacing the original atmosphere with a reducing atmosphere or a mixture of an inert atmosphere and reducing atmosphere, wherein the mixture of an inert atmosphere and a reducing atmosphere contains about 0.5 to about 99% by volume reducing atmosphere.

17. The method of claim 1, wherein removing and replacing is done by flushing an original atmosphere under vacuum and replacing the original atmosphere with a reducing atmosphere or a mixture of an inert atmosphere and reducing atmosphere, wherein the mixture of an inert atmosphere and a reducing atmosphere contains about 0.5 to about 99% by volume reducing atmosphere.

* * * * *

UNITED STATES PATENT AND TRADEMARK OFFICE
CERTIFICATE OF CORRECTION

PATENT NO.       : 7,645,458 B2
APPLICATION NO. : 10/614448
DATED            : January 12, 2010
INVENTOR(S)      : Lawrence A. Shimp It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 721 days.

Signed and Sealed this

Sixteenth Day of November, 2010

David J. Kappos
*Director of the United States Patent and Trademark Office*